United States Patent
Armstrong et al.

(10) Patent No.: US 8,016,752 B2
(45) Date of Patent: Sep. 13, 2011

(54) PUNCTURABLE CATHETER

(75) Inventors: Joseph R. Armstrong, Flagstaff, AZ (US); Edward H. Cully, Flagstaff, AZ (US); Keith M. Flury, Flagstaff, AZ (US); Michael J. Vonesh, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 10/402,083

(22) Filed: Mar. 28, 2003

(65) Prior Publication Data

US 2004/0193139 A1    Sep. 30, 2004

Related U.S. Application Data

(63) Continuation-in-part of application No. 10/346,977, filed on Jan. 17, 2003, now abandoned.

(51) Int. Cl.
  *A61B 1/12*  (2006.01)
  *A61M 29/00*  (2006.01)

(52) U.S. Cl. .................... 600/156; 604/102.03

(58) Field of Classification Search ............... 604/93.01, 604/96.01, 263, 523, 524, 526, 527, 102.03, 604/526–27, 43, 510, 525, 97.01, 102.02, 604/103.04, 103.09, 160, 166.01, 264; 606/192, 606/194; 600/156, 128, 104, 124, 153, 116
See application file for complete search history.

(56) References Cited

U.S. PATENT DOCUMENTS

| | | | |
|---|---|---|---|
| 3,105,492 A | 10/1963 | Jeckel et al. | |
| 3,953,566 A | 4/1976 | Gore | |
| 4,187,390 A | 2/1980 | Gore | |
| 4,235,231 A | 11/1980 | Schindler et al. | |
| 4,552,554 A | 11/1985 | Gould et al. | |
| 4,574,477 A | 3/1986 | Lemkin et al. | |
| 4,601,713 A | 7/1986 | Fuqua | 604/280 |
| 4,732,152 A | 3/1988 | Wallsten et al. | |
| 4,762,129 A | 8/1988 | Bonzel | 128/334 |
| 4,877,661 A | 10/1989 | House et al. | 428/34.9 |
| 4,988,356 A | 1/1991 | Crittenden et al. | 606/192 |

(Continued)

OTHER PUBLICATIONS

MSN Encarta Definition of "catheter": http://encarta.msn.com/encnet/features/dictionary/DictionaryResults.aspx?refid=1861595493.

(Continued)

*Primary Examiner* — Kevin C Sirmons
*Assistant Examiner* — Andrew M Gilbert
(74) *Attorney, Agent, or Firm* — Wayne D. House

(57) ABSTRACT

A catheter provided with a guidewire catheter lumen having a thin covering that is easily punctured by a guidewire at virtually any desired point along the catheter length. The thin covering may be integral with the catheter shaft, or may be a separate component that covers only the portion of the catheter shaft immediately adjacent the outer portion of the guidewire lumen, or may be a thin tubular construct that surrounds the entire catheter shaft. The covering is preferably relatively translucent, allowing for good visualization of the location of the end of the guidewire to enable puncturing of the covering at the desired location along the length of the catheter shaft. The covering is also preferably tear resistant at puncture sites. The catheter shaft is preferably made of a material having a color that provides good visibility against an operating field, and more preferably is phosphorescent either entirely or in part. Materials suitable for the catheter shaft are polymeric materials well known in the art; the catheter shaft may optionally be provided with metallic stiffening components such as wires or hypotubes along all or part of the catheter length.

8 Claims, 8 Drawing Sheets

U.S. PATENT DOCUMENTS

| | | | | |
|---|---|---|---|---|
| 5,024,234 A | * | 6/1991 | Leary et al. | 600/467 |
| 5,030,210 A | | 7/1991 | Alchas | 604/247 |
| 5,061,273 A | | 10/1991 | Yock | 606/194 |
| 5,102,403 A | | 4/1992 | Alt | 604/280 |
| 5,107,852 A | * | 4/1992 | Davidson et al. | 600/585 |
| 5,135,535 A | | 8/1992 | Kramer | 606/194 |
| 5,171,222 A | | 12/1992 | Euteneuer et al. | 604/102 |
| 5,195,978 A | | 3/1993 | Schiffer | 604/161 |
| 5,205,822 A | | 4/1993 | Johnson et al. | 604/96 |
| 5,273,042 A | | 12/1993 | Lynch | |
| 5,324,269 A | | 6/1994 | Miraki | 604/160 |
| 5,334,147 A | | 8/1994 | Johnson | 604/96 |
| 5,334,153 A | | 8/1994 | McIntyre et al. | |
| 5,334,169 A | | 8/1994 | Brown et al. | |
| 5,336,184 A | * | 8/1994 | Teirstein | 604/103.04 |
| 5,364,353 A | | 11/1994 | Corfitsen et al. | |
| 5,380,283 A | | 1/1995 | Johnson | 604/96 |
| 5,380,290 A | * | 1/1995 | Makower et al. | 604/164.01 |
| 5,389,087 A | | 2/1995 | Miraki | 604/247 |
| 5,395,335 A | | 3/1995 | Jang | 604/102 |
| 5,413,559 A | | 5/1995 | Sirhan et al. | |
| 5,425,723 A | | 6/1995 | Wang | 604/280 |
| 5,445,646 A | | 8/1995 | Euteneuer et al. | 606/198 |
| 5,458,613 A | | 10/1995 | Gharibadeh et al. | |
| 5,466,222 A | | 11/1995 | Ressemann | |
| 5,472,423 A | | 12/1995 | Gronauer | |
| 5,472,425 A | | 12/1995 | Teirstein | 604/102 |
| 5,476,589 A | | 12/1995 | Bacino | |
| 5,489,271 A | | 2/1996 | Andersen | 604/102 |
| 5,531,700 A | | 7/1996 | Moore et al. | |
| 5,534,007 A | | 7/1996 | St. Germain et al. | 606/108 |
| 5,571,135 A | | 11/1996 | Fraser et al. | |
| 5,573,520 A | * | 11/1996 | Schwartz et al. | 604/526 |
| 5,578,009 A | | 11/1996 | Kraus et al. | |
| 5,591,194 A | | 1/1997 | Berthiaume | 606/192 |
| 5,647,857 A | | 7/1997 | Anderson et al. | 604/264 |
| 5,662,703 A | | 9/1997 | Yurek et al. | |
| 5,690,644 A | | 11/1997 | Yurek et al. | |
| 5,709,658 A | | 1/1998 | Sirhan et al. | |
| 5,718,680 A | | 2/1998 | Kraus et al. | |
| 5,752,932 A | | 5/1998 | Ellis et al. | 604/96 |
| 5,752,934 A | * | 5/1998 | Campbell et al. | 604/96.01 |
| 5,788,707 A | | 8/1998 | Del Toro et al. | |
| 5,807,355 A | * | 9/1998 | Ramzipoor et al. | 604/526 |
| 5,846,259 A | | 12/1998 | Berthiaume | |
| 5,879,794 A | | 3/1999 | Korleski et al. | |
| 5,919,164 A | | 7/1999 | Andersen | 604/102 |
| 5,968,012 A | | 10/1999 | Ren | |
| 5,972,441 A | * | 10/1999 | Campbell et al. | 428/34.1 |
| 5,993,460 A | | 11/1999 | Beitelia et al. | 606/108 |
| 6,016,848 A | | 1/2000 | Egres, Jr. | 138/137 |
| 6,027,779 A | | 2/2000 | Campbell et al. | |
| 6,056,719 A | | 5/2000 | Mickley | 604/96 |
| 6,059,813 A | | 5/2000 | Vrba et al. | 606/198 |
| 6,095,990 A | | 8/2000 | Parodi | 600/585 |
| 6,099,496 A | | 8/2000 | Berthiaume et al. | 604/96 |
| 6,107,004 A | | 8/2000 | Donadio, III | |
| 6,159,565 A | | 12/2000 | Campbell et al. | 428/35.7 |
| 6,200,305 B1 | | 3/2001 | Berthiaume et al. | 604/509 |
| 6,203,558 B1 | | 3/2001 | Dusbabek et al. | 606/198 |
| 6,238,410 B1 | | 5/2001 | Vrba et al. | |
| 6,273,899 B1 | | 8/2001 | Kramer | 606/194 |
| 6,299,595 B1 | | 10/2001 | Dutta et al. | 604/96 |
| 6,398,799 B2 | | 6/2002 | Kramer | 606/194 |
| 6,423,032 B2 | | 7/2002 | Parodi | |
| 6,447,540 B1 | | 9/2002 | Fontaine et al. | 623/1.12 |
| 6,458,099 B2 | | 10/2002 | Dutta et al. | |
| 6,544,278 B1 | | 4/2003 | Vrba et al. | |
| 6,589,207 B1 | | 7/2003 | El-Nounou | |
| 6,673,102 B1 | | 1/2004 | Vonesh et al. | |
| 6,783,522 B2 | | 8/2004 | Fischell | 604/537 |
| 6,929,634 B2 | | 8/2005 | Dorros | |
| 2001/0031979 A1 | | 10/2001 | Ricci | |
| 2002/0065550 A1 | | 5/2002 | Smith | |
| 2002/0077654 A1 | | 6/2002 | Javier, Jr. et al. | |
| 2002/0082556 A1 | | 6/2002 | Cioanta et al. | |
| 2003/0050661 A1 | | 3/2003 | Kramer | 606/194 |
| 2004/0122509 A1 | | 6/2004 | Brodeur | |

OTHER PUBLICATIONS

Definition of "film" Compact English Oxford Dictionary: definition of "film" http://www.askoxford.com/concise_oed/film?view=uk.

* cited by examiner

PUNCTURABLE CATHETER

CROSS REFERENCE TO RELATED APPLICATIONS

This application is a continuation-in-part of application Ser. No. 10/346,977 filed Jan. 17, 2003 now abandoned.

FIELD OF THE INVENTION

The present invention relates to the field of catheters for use with guidewires, and more particularly to such catheters intended for the delivery of a therapeutic agent or device.

BACKGROUND OF THE INVENTION

A variety of different therapies can be delivered within the human body by catheter devices. Therapeutic devices such as dilation balloons, stents, and embolic filters, and therapeutic agents such as drugs and radiation sources, may be positioned at or near the distal end of the catheter for delivery to a desired site within the body. The proximal end of the catheter is considered to be the end that remains outside of the body, manipulated by the medical practitioner.

To aid in positioning of the distal end of the catheter within the body, typically the distal end of a guidewire is first navigated to the treatment area. After the guidewire has been positioned, the wire can then be used to guide the distal end of the catheter into place. Additionally, a guide catheter may be used to further facilitate the positioning of the guidewire and/or delivery catheter. The interaction between the guidewire and the catheter is critical, as the physician needs to easily track the distal end of the catheter along the path of the guidewire. A number of interaction issues can arise, including but not limited to, having to use more than one person, having to use a long wire, having the advancement of the catheter affect the position of the wire, having the catheter not able to track the wire through tortuous anatomy, having excessive friction between the catheter and the wire, and having a difference between the amount of axial motion applied to the proximal end of the catheter and the amount of axial movement at the distal end of the catheter.

In various attempts to address these issues, a number of catheter designs have been introduced that have defined the interaction between the guidewire and the catheter. Two of the primary applications of catheter systems are percutanous transluminal coronary angioplasty (PTCA) and coronary stent delivery. Two main types of catheter designs, over-the-wire (OTW) and rapid-exchange (RX), dominate these applications. Each of these designs has its advantages and disadvantages. OTW catheters track over their entire length on a guidewire, which allows them to follow the wire easily and allows the direct transmission of longitudinal force over the guidewire. Additionally, these catheters allow for guidewires to be exchanged once the catheter has been advanced into position, which may be desirable when different guidewire attributes (e.g., tip curvature or radiopaque markers) are needed. However, these systems require the use of a long guidewire (e.g., 300 cm in length) and cannot be effectively operated by one person.

RX catheters typically use shorter guidewires (e.g., 180 cm in length) which allow the catheter to be operated by a single physician. The physician is able to hold the guide catheter and guidewire with one hand while using his other hand to advance or retract the catheter along the guidewire. However, because the entire length of the RX catheter does not slide over the guidewire, the direct transmission of longitudinal force along the path of the guidewire may be compromised, and wire exchange can not be performed once the proximal catheter guidewire port is advanced into the patient.

Among various catheter designs intended for stent delivery is a system taught by U.S. Pat. No. 5,534,007 to St. Germain et al. This system includes a tubular exterior sleeve with an adjustable length section that, under axial compression, shortens via corrugations to cause another sleeve at the distal end of the catheter to be withdrawn in a proximal direction, releasing the stent. The overall length of the catheter remains the same during the axial compression of the exterior sleeve, and in particular, the length of the guidewire lumen is not adjustable.

U.S. Pat. Nos. 5,334,147 and 5,380,283 to Johnson teach the construction of a balloon catheter having a proximal portion that includes an aperture through the wall of the catheter into the guidewire lumen. The aperture is covered by a frangible wall (e.g., a thin-walled tube sealed to the catheter body in a position to cover the aperture portion). The frangible wall may be punctured by a guidewire, allowing the guidewire to exit the catheter guidewire lumen via the aperture.

U.S. Pat. No. 5,472,425 to Teirstein describes a catheter having a guidewire lumen covered by a rupturable membrane that extends along substantially the entire length of the catheter, whereby the membrane may be intentionally punctured at any desired location by the guidewire. The use and general construction of the catheter are related, although no materials or specific constructions for the rupturable membrane are taught.

SUMMARY OF THE INVENTION

The present invention relates to a catheter provided with a guidewire catheter lumen having a thin covering that is easily punctured by the back end (i.e., the proximal end) of a guidewire at virtually any desired point along the catheter length. The thin covering may be integral with the catheter shaft, or may be a separate component that covers only the portion of the catheter shaft immediately adjacent the outer portion of the guidewire lumen, or may be a thin tubular construct that surrounds the entire catheter shaft. The covering is preferably adequately translucent to allow for good visualization of the location of the back end of the guidewire in order to enable puncturing of the covering at the desired location along the length of the catheter shaft. The catheter shaft is preferably made of a material having a color that provides good visibility against an operating field, and more preferably is luminous or phosphorescent either entirely or in part. Materials suitable for the catheter shaft are polymeric materials well known in the art; the catheter shaft may optionally be provided with metallic stiffening components such as wires, wire braids or hypotubes along all or part of the catheter length.

In a preferred embodiment, the thin covering is made from a thin tape of porous expanded polytetrafluoroethylene (ePTFE) helically wrapped about the exterior of a catheter shaft. Most preferably, the wrapping is accomplished in two opposing directions parallel to the length of the catheter shaft, resulting in a bias-ply construction. This thin covering offers good transparency and is easily punctured by the end of a guidewire, and yet is resistant to tearing at the puncture site.

Other materials may be used for the puncturable thin covering, including polyethylene terephthalate (PET). These materials may also offer good translucency, but may be less tear resistant than the helically wrapped ePTFE thin coverings.

The thin covering (either integral with the catheter shaft or a separate covering) may optionally be provided with a multiplicity of small, pre-formed openings through the thickness of the covering to allow for passage of the back end of a guidewire through any of these openings. The openings would preferably be arranged in a single line extending directly above the guidewire lumen.

The thin covering may optionally be in the form of a braid or helically-wound filaments that allow the guidewire to be passed through any of the multiplicity of openings or interstices that exist between adjacent filaments of the braid or winding. The braid or winding may be of either various polymeric or metallic materials. The braid or winding may be exposed around the entire exterior of the catheter shaft or alternatively may be exposed over only the side of the guidewire lumen closest to the exterior of the catheter shaft.

For many embodiments, the guidewire lumen is in the form of a slot made into the catheter shaft, with the slot provided with the thin covering. Preferably, the slot extends for most or even all of the length of the catheter shaft. It may optionally extend through a balloon or other device located at the distal end of the catheter. The slot is covered with by a thin tubular covering that coaxially encloses the entire catheter shaft or alternatively a strip of thin tape-like covering material that covers the slot and is adhered to the surface of the catheter shaft immediately adjacent both sides of the slot. A multiplicity of pre-formed openings may be provided through the thin covering as noted above. Also as noted above, the slot covering material may take the form of a braid or winding of filaments. This braid or winding of filaments may optionally be covered with a thin polymeric tube except for the filaments immediately over the top of the slot which preferably remain exposed and allow for passage of the end of a guidewire through any interstice between adjacent filaments.

Other embodiments using the catheter shaft may be provided with a puncturable tubular form inserted into the slot. This tubular form may be made with filaments braided into the tubular form, or a tubular form made of helically wound filaments or from a thin polymeric material, with the tube having an inside diameter adequately large to accommodate a guidewire of the desired size. These tubes are fitted and secured into the slot formed into the catheter shaft, with the result that the outer surface of the braided or helically wound tube covers the exposed part of the slot and allows for the back end of a guidewire contained within the tube to be passed through any interstice between adjacent filaments of the braided or helically wound tube. When the tubular form is made from the thin polymeric material, the resulting tube inserted into the catheter shaft slot is puncturable at any desired location by the back end of a guidewire.

In addition to being puncturable by the back end of the guidewire, the guidewire catheter lumen may optionally be made to be adjustable in length. The adjustable length catheter guidewire lumen is the conduit, or catheter, or tube, or space that contains the guidewire or provides a space for the passage of a guidewire therethrough. The space may be adjustable in length, as will be further described.

By adjustable length is meant that the length of the adjustable length guidewire catheter lumen may be changed by the application of easily applied manual axial force. In its axially extended or fully lengthened state, the adjustable length guidewire catheter lumen is at least 10% longer than when in the axially compressed, fully shortened state. More preferably, the adjustable length guidewire catheter lumen is adjustable by an amount of at least about 20%, or 30%, or 40%, or 50%, or 75%, or 100%, or 200%, or 400%, or 1000%, or 2000%.

The adjustable length guidewire catheter lumen is adjustable in length by virtue of being scrunchable. This means that this tubular component is easily shortened in length under axial force, without telescoping as by the successive sliding of overlapped concentric tubular sections. Various means of providing a scrunchable tube for use as the adjustable length guidewire catheter lumen include the provision of corrugations (i.e., wrinkles, or accordion pleats or folds), or by the use of a porous tube that compresses axially by reduction in total void space. These are further described below.

Suitable materials for the adjustable length lumen include ePTFE, polyethylene terephthalate (PET), polyamide, or other thermoplastic or thermoset polymers, or other such relatively inelastic materials. Alternatively, an elastomeric material may be used for the adjustable length lumen, which materials elongate by the application of an extending axial force. The term "elastomeric" is intended to describe a condition whereby a polymer displays stretch and recovery properties similar to an elastomer, although not necessarily to the same degree of stretch and/or recovery.

The ability of the catheter to be punctured by the back end of a guidewire at any desired location along the length of the puncturable section of the catheter allows the catheter assembly to be used effectively as desired in either OTW or RX mode.

DETAILED DESCRIPTION OF THE INVENTION

Figure 1A:
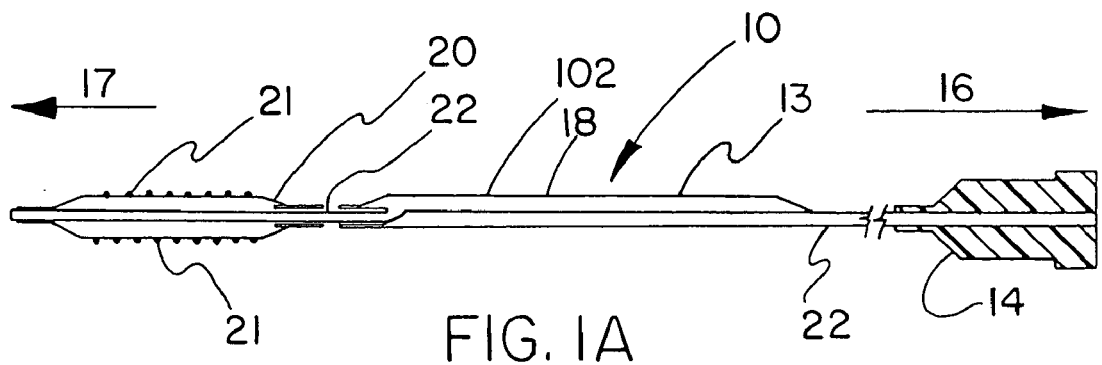
FIG. 1A shows a longitudinal cross section of a catheter having a puncturable guidewire lumen covering.

FIGS. 1A-1H describe the catheter 10 of the present invention provided with a thin, puncturable cover 102 over the guidewire lumen 18. Typically, catheter 10 may include devices such as a catheter balloon 20 and/or stent 21 at its distal end 17 and a hub 14 at the proximal end 16. As shown by FIGS. 1A-1H, the thin, puncturable cover 102, in this instance a thin-walled a thin tubular sheath 13 (forming guidewire lumen 18) designed to be punctured by the back end of a guidewire 19, may be placed coaxially about the inflation lumen 22. The length of the thin tubular sheath 13 may extend over all or part of the length of catheter shaft.

After feeding guidewire 19 through the distal section of the guidewire lumen 18 and into the thin-walled tubular sheath 13, the physician may chose any desired location along the length of thin-walled tubular sheath 13 at which to puncture the thin, puncturable cover 102 with the guidewire 19. In this fashion the physician may select his preferred length of the guidewire lumen 18.

Figure 1B:
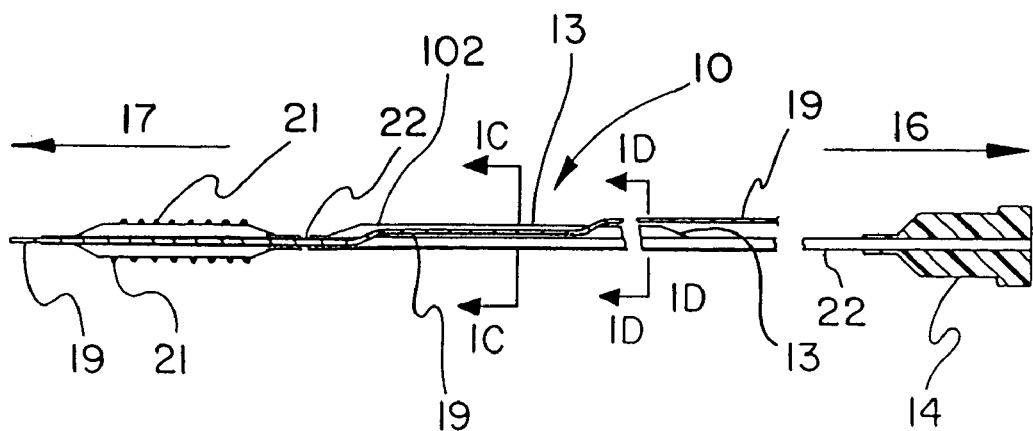
FIG. 1B shows a longitudinal cross section of the catheter of FIG. 1A in use with the catheter, the guidewire having punctured the puncturable guidewire lumen covering.
Figure 1C:
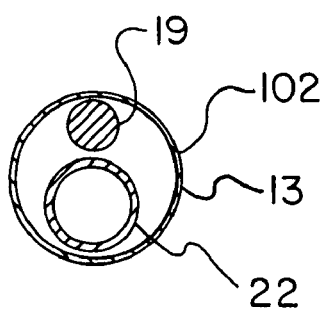
FIGS. 1C and 1D show transverse cross sections of the catheter of FIG. 1B with the guidewire within and without the puncturable section.
Figure 1D:
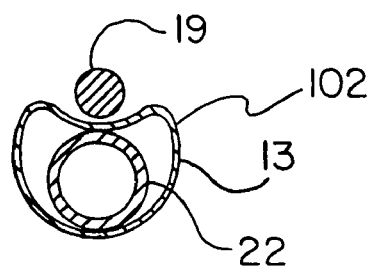

FIG. 1A shows a longitudinal cross section of a catheter 10 having a puncturable guidewire lumen covering 102, while FIG. 1B shows a longitudinal cross section of the catheter of FIG. 1A in use with the guidewire 19, the guidewire having punctured the puncturable covering 102. FIGS. 1C and 1D show, respectively, transverse cross sections of the catheter of FIG. 1B with the guidewire 19 within and outside of the puncturable section 102.

Figure 1E:
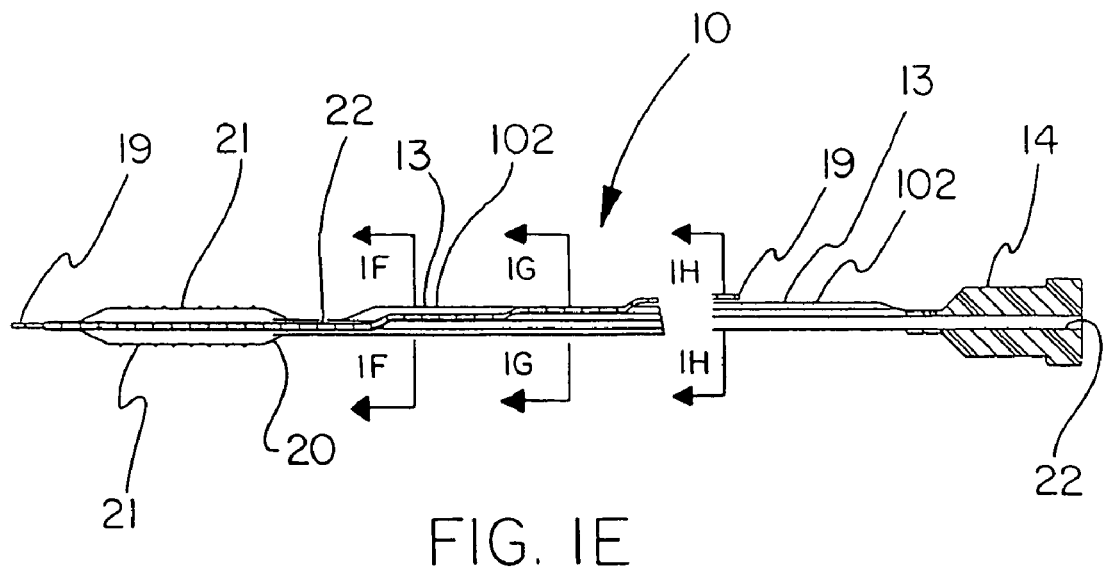
FIG. 1E shows a longitudinal cross section of a catheter that is a variation of the design shown in FIGS. 1A and 1B wherein the guidewire operates in a slot provided in the exterior wall of a lumen of the catheter.
Figures 1F, 1G:
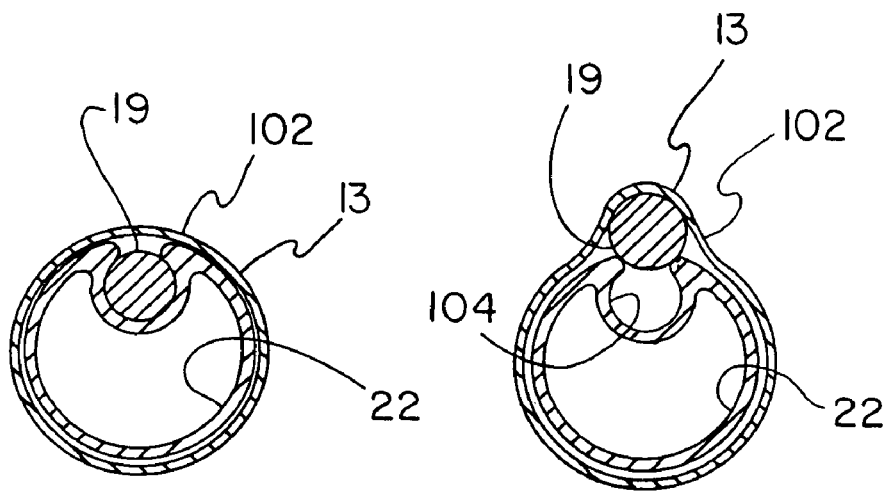
FIGS. 1F, 1G and 1H show transverse cross sections taken at three different locations along the length of the catheter shown in FIG. 1E.
Figure 1H:
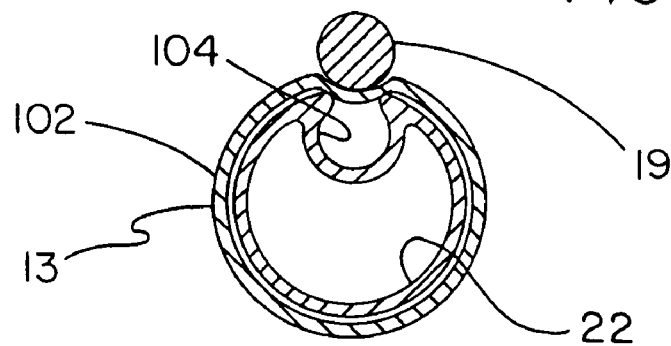

FIG. 1E shows a longitudinal cross section of a catheter that is a variation of the design shown in FIGS. 1A and 1B wherein the guidewire operates in a slot 104 provided in the exterior wall of a lumen of the catheter. It is apparent that the thin, puncturable cover 102 may be provided only over this slot portion and is not required to enclose the entire circumference of the inner catheter. FIGS. 1F, 1G and 1H show transverse cross sections taken at three different locations along the length of the catheter shown in FIG. 1E.

The puncturable guidewire lumen may be made in a variety of ways.

Figure 2A:
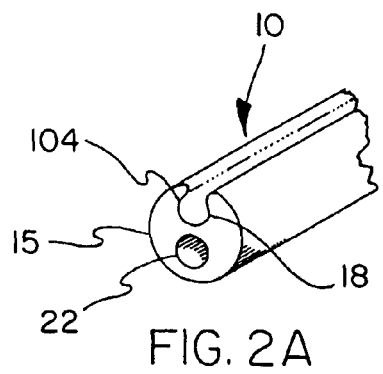
FIG. 2A shows a perspective view of a preferred slotted catheter shaft.

In a preferred embodiment, catheter 10 including inflation lumen 22 and guidewire lumen 18 is made using a catheter shaft 15 as shown in the perspective view of FIG. 2A wherein guidewire lumen 18 is in the form of a slot 104. The catheter shaft 15 may be made in this form by extrusion (using any known polymeric material suitable for the application), or may alternatively be extruded with fully enclosed lumens and then have the extruded material covering the guidewire lumen skived away. Preferred materials will be of a color offering good contrast with the operational field, and most preferably are fluorescent or phosphorescent.

Optionally, such a catheter shaft may be stiffened along all or part of its length as necessary by the inclusion of stiffening wires running parallel to the longitudinal axis of the catheter, or by adding a tubular metal reinforcing braid to the catheter shaft, or by inserting a length of metal hypotube, tubular braid or helically wound wire into the inflation lumen 22. These stiffening methods may be used in combination if desired. For simplicity, these well-known stiffening methods are not shown in the figures.

If it is desired to use a hypotube to stiffen only a portion of the length of the catheter shaft, it may be desirable to cut a helically-oriented slot through the wall of the end of the hypo tube that will be located within the length of the catheter shaft to reduce the abrupt stiffness transition of the stiffened section to the unstiffened section.

Figure 2B:
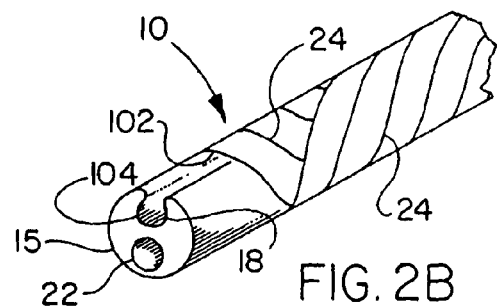
FIG. 2B is a perspective view of the preferred slotted catheter shaft of FIG. 2A provided with a helical wrap of a polymeric tape that forms a puncturable thin cover over the slot.

As shown by the perspective view of FIG. 2B, the slotted catheter shaft 15 is provided with a helically-wrapped covering of tape 24. Preferably, the wrapping is applied in two layers wherein adjacent wrappings have overlapping edges and the second layer is applied over the first with an opposite pitch, meaning that the two wrappings are applied beginning from opposite ends of the catheter shaft 15. The use of the two layers of tape 24 wrapped from opposing directions results in a strong covering that is resistant to tearing following puncture by the guidewire back end.

While a variety of thin, flexible polymer materials such as polyethylene, polypropylene, polyamide, polyethylene terephthalate, etc. may be used for the tape 24. Porous polymers, optionally provided with a thin, non-porous coating, may be advantageously used because of their excellent flexibility. Tape 24 is most preferably made from a thin porous expanded PTFE (ePTFE) film that has been provided with a porous or non-porous coating of a thermoplastic such as a thermoplastic fluoropolymer, preferably fluorinated ethylene propylene (FEP). ePTFE films are generally made as taught by U.S. Pat. Nos. 3,953,566 and 4,187,390 to Gore. Most preferred ePTFE films for the present application are taught by U.S. Pat. No. 5,476,589 to Bacino. The construction of thin, helically-wrapped tubes from ePTFE films and thermoplastic-coated ePTFE films, and the method of providing the coating onto the ePTFE films, are taught by U.S. Pat. No. 6,159,565 to Campbell et al.

An example of a helically-wrapped catheter shaft as shown by FIG. 2B was made using an FEP-coated ePTFE tape. The tape had a width of about 6 mm and a thickness of about 0.005 mm. The ePTFE had mean fibril length of about 50 microns and a bulk density of about 0.5 g/cc. The ePTFE film was provided with a non-porous coating of FEP on one side. After the coated film was cut into a narrow tape, the tape was helically wrapped onto a stainless steel mandrel of diameter larger that the outside diameter of the chosen catheter shaft. The first layer of the wrapping was applied with the FEP coated side of the tape facing away from the mandrel and the second layer was wrapped in the opposite direction from the first with the coating facing toward the mandrel and first layer. The wrapped mandrel was then heated for about 8 minutes in a convection oven set at 320° C. to melt-bond the helically-wrapped layers of the tube together. Following removal from the oven and cooling to about room temperature, the helically-wrapped tube was removed from the mandrel and fitted over a length of the desired catheter shaft 15 that was shorter than the length of the helically-wrapped tube. The opposite ends of the helically wrapped tube were gripped using pliers and tension was applied to cause the helically-wrapped tube to elongate and reduce in diameter, thereby tightly conforming to the outer surface of the catheter shaft. The ends of the helically-wrapped tube were adhered to the outer surface of the catheter shaft using a cyanoacrylate adhesive. The ends of the covered catheter shaft 15 were then transversely cut to the desired length with a sharp blade. If desired, the hub component typically fitted to the proximal end of the catheter shaft may be fitted over the helical wrap.

The thickness of the thin tubular tape covering 102 was determined to be about 0.012 mm by measuring the diameter of the catheter shaft at 90 degrees to the orientation of the slot 104 using a laser micrometer both before and after the application of the helically-wrapped covering.

The covered catheter 10 that resulted from this process retained the good flexibility of the precursor catheter shaft 15 prior to covering. When a guidewire 19 was inserted into the guidewire lumen 18, the thin cover 102 exhibited good transparency, meaning that the back end of the guidewire 19 was visible to the unaided eye as it passed through the length of the guidewire lumen 18. It was not difficult to stop the progression of the guidewire back end at a desired point along the length of the guidewire lumen, and by bending the catheter with the guidewire slot oriented to the outside of the bend, the covering 102 was readily punctured by the back end of the guidewire 19. When a large portion of the length of the guidewire was pulled through the puncture site, the puncture site exhibited no sign of tearing or of appreciable enlargement of the puncture.

Figure 2C:
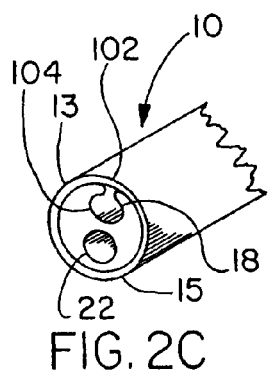
FIG. 2C is a perspective view of the preferred slotted catheter shaft of FIG. 2A provided with a puncturable thin cover in the form of a thin tubular sheath.

FIG. 2C is a perspective view of a catheter 10 including a tubular sheath 13 for use as the thin puncturable cover 102 over slot 104. The sheath may be in the form of a thin extruded tube of, for example, PET. It may be applied similarly to the above-described helically-wrapped tube using a tubular sheath 13 of slightly larger inside diameter than the outside diameter of the catheter shaft 15 to be covered. The outer surface of the catheter shaft 15 may be provided with a thin coating of a suitable adhesive if desired, after which the thin tubular sheath 13 is fitted over the catheter shaft 15 and tensioned to cause it to elongate and reduce in diameter to conform to the outer surface of the catheter shaft 15. Sheath 13 may also be made from a shrink tubing that is heated after being fitted about the outer surface of the catheter shaft 15 to cause it to conform thereto.

Figure 2D:
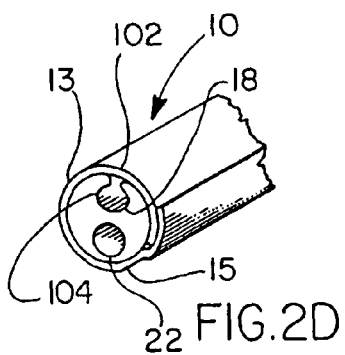
FIG. 2D is a perspective view of the catheter shaft of FIG. 2C wherein the thin tubular sheath is formed by a cigarette wrap.

FIG. 2D is a perspective view of the catheter 10 of FIG. 2C wherein the thin tubular sheath is formed by a cigarette wrap, wherein the braid-covered catheter shaft is additionally covered by an adequately long strip of thin polymeric material that has a width equal to or slightly greater than the circumference of the braid covered catheter shaft. This strip is wrapped around the catheter shaft as shown and adhered by thermal bonding or by the use of a suitable adhesive.

Figure 2E:
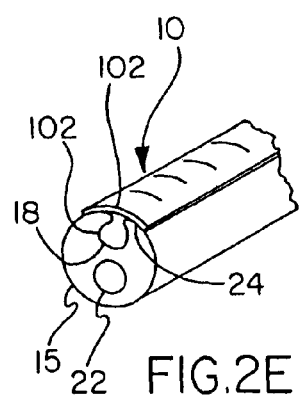
FIG. 2E is a perspective view of the preferred slotted catheter shaft of FIG. 2A provided with a puncturable thin cover in the form of a strip or tape of a polymeric material adhered over the surface of the catheter shaft immediately adjacent to both sides of the slot.
Figure 2G:
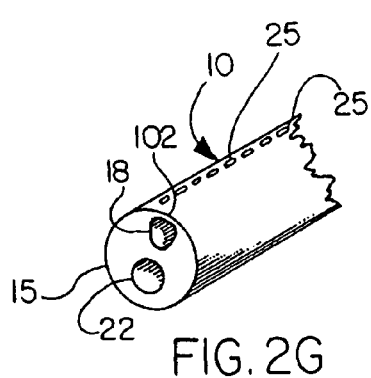
FIG. 2G is a perspective view of an alternative embodiment wherein the thin cover over the guidewire lumen is provided with a multiplicity of pre-formed openings which allow passage of the back end of a guidewire through any opening chosen by the user.
Figure 2F:
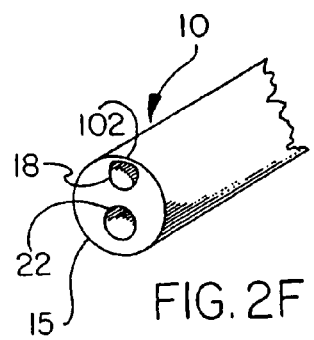
FIG. 2F is a perspective view of an alternative embodiment wherein the puncturable guidewire lumen covering is integral with the catheter shaft.

Another alternative for the puncturable thin cover 102 is shown in the perspective view of FIG. 2E wherein a thin tape 24 is adhered to the outer surface of the catheter shaft 15 adjacent to the edges of slot 104. In another embodiment, the guidewire lumen 18 may be extruded or otherwise formed to have an integral, thin, puncturable covering 102 as shown by the perspective view of FIG. 2F. FIG. 2G is a perspective view of the catheter 10 of FIG. 2F wherein pre-formed openings 25 are formed through the thin puncturable cover 102 to allow passage of the back end of a guidewire through any pre-formed opening 25 chosen by the user. It is apparent that these pre-formed openings 25 may be used with many of the various described embodiments.

Figure 3A:
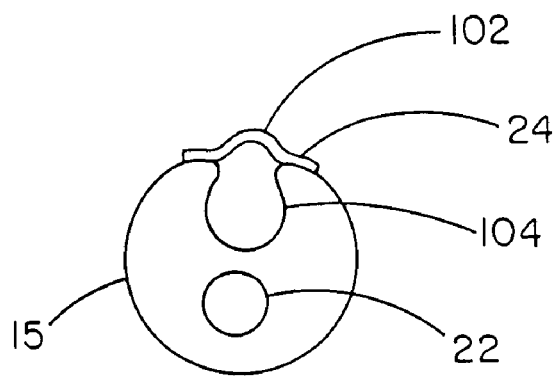
FIGS. 3A-3C are transverse cross sectional views showing variations of the embodiment described by FIG. 2E
Figure 3B:
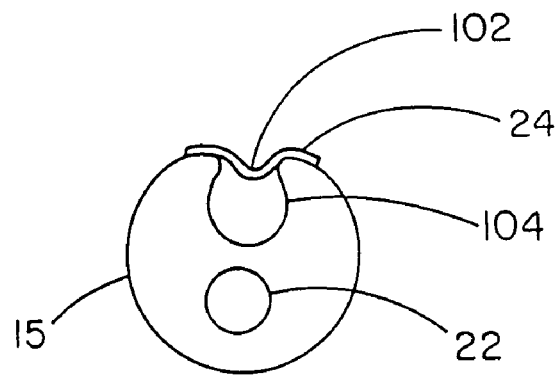
Figure 3C:
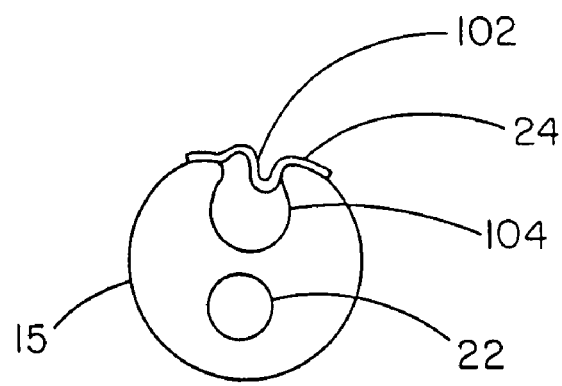

FIGS. 3A-3C show transverse cross sectional views that represent a variation on the embodiment of FIG. 2E. As shown by FIG. 3A, tape cover 24 may be provided so as to increase the space available in the guidewire slot 104 by applying the tape so that it bridges the slot with additional tape width, resulting in the raised aspect shown by this thin puncturable cover 102. This can allow for the use of a larger guidewire if desired. When slot 104 is unoccupied by a guidewire, the thin and flexible tape 24 may take on a non-uniform appearance, giving the guidewire lumen and thin puncturable cover 102 an irregular cross section as shown by FIGS. 3B and 3C. It is apparent that the appearance of each of these three transverse cross-sections may exist at different locations along the length of the same catheter.

The puncturable cover 102 may also be made using threads, wires or other filaments. For example, threads may be wound around a slotted catheter shaft 15 in various desired patterns to form a covering over a guidewire lumen 18 that effectively contains a guidewire 19 but allows the back end of the guidewire to be passed through any of the multiplicity of spaces between adjacent threads of the wrapped covering. The threads may, for example, be provided as a helically-wrapped pattern, a braided pattern or a knit (e.g. warp knit) pattern. By orienting the threads in close proximity to one another, the guide wire will preferentially stay within a lumen of which the thread defines a portion of the wall. However, the end of the wire can be maneuvered to exit this lumen between the threads. By using a wound thread, the structure is never damaged allowing the catheter to be reused multiple times. By controlling the spacing between adjacent threads, the ease of which the end of the wire exits the lumen may be altered. Preferentially, small diameter threads can be used, for example, with diameters from 0.012 to 0.5 mm. Any variety of thread materials may be used, included common thermoplastic (e.g., polyamide, polypropylene, polyester, etc), thermosets, fluoroplastics (e.g., ePTFE) or various metal wires including stainless steels and nitinol.

Figure 4A:
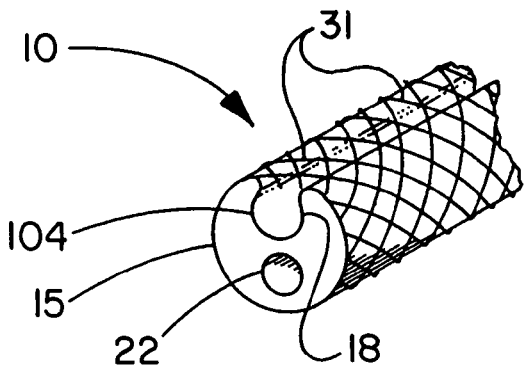
FIG. 4A is a perspective view of the preferred slotted catheter shaft of FIG. 2A provided with a puncturable thin cover in the form of a braid.

As shown by the perspective view of FIG. 4A, a catheter shaft 15 is over-braided with filaments 31. The braid may have numerous configurations including, but not limited to, number of filaments, pick count and pitch angle. As well, filaments 31 may be of various cross sections such as round, square or rectangular.

Figure 4B:
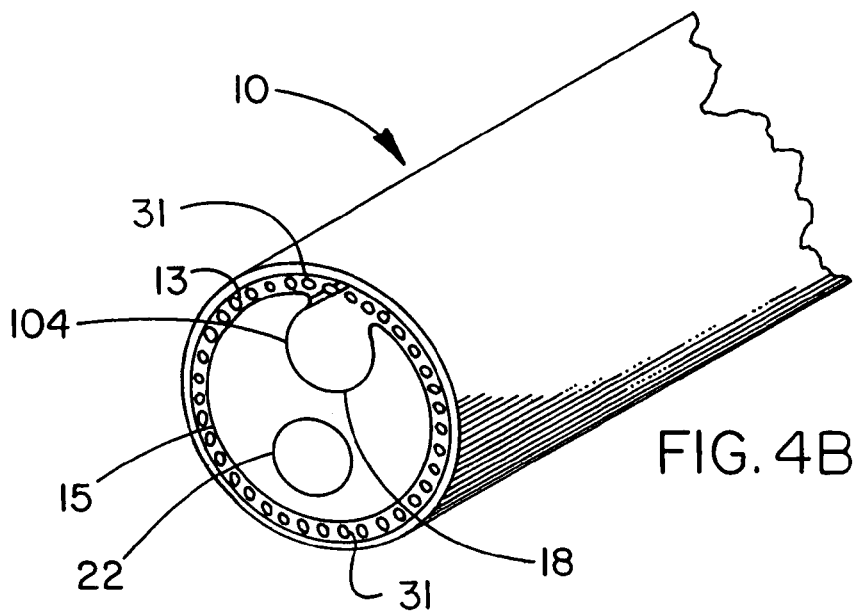
FIG. 4B is a perspective view of the braid-covered catheter shaft of FIG. 3A further provided with a thin exterior tubular sheath over the braid.
Figure 4C:
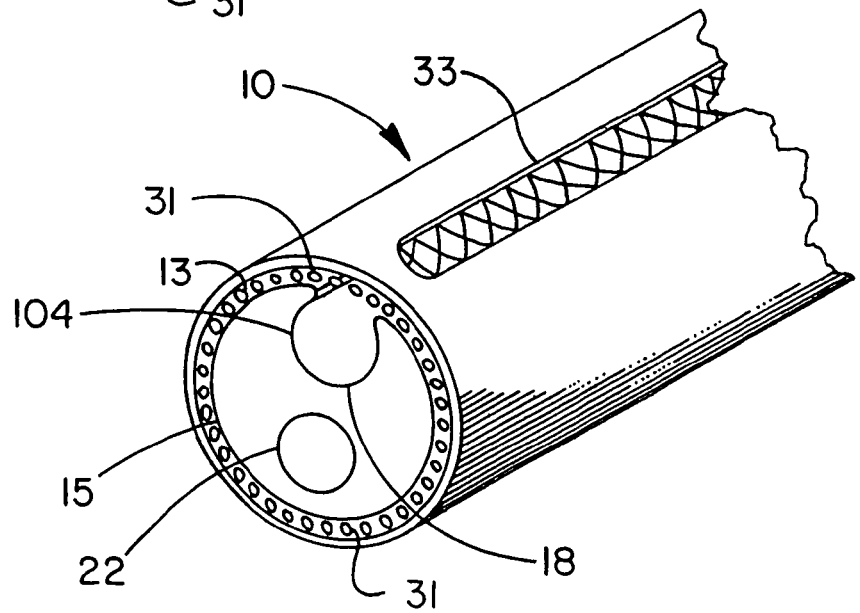
FIG. 4C is a perspective view of the braid-and-sheath covered catheter shaft of FIG. 3B wherein the portion of the sheath covering the catheter slot has been removed.

FIG. 4B shows a preferred embodiment wherein catheter 10 of FIG. 4A is provided with an outer sheath 13 applied over catheter shaft 15 and braid 31 and attached by any of various methods such as heat or adhesive. Following the addition of sheath 13, an appropriately-sized mandrel is inserted into the guidewire lumen 18. The catheter is mounted in a laser (e.g., a 20 watt $CO^2$ laser, Applied Laser Technology, Beaverton Oreg.) with the laser beam directed to slot 104. The laser is used to ablate the polymer material of sheath 13 covering slot 104 along the desired length of the catheter 10, resulting in cutaway slot 33 through sheath 13 exposing slot 104 beneath braid 31. The laser power parameters are such that the polymer material of sheath 13 is ablated yet metallic braid filaments 31 are left undamaged. The indwelling mandrel effectively blocks the laser energy from damaging the opposite side of the catheter shaft 15. The resultant catheter 10 is left with a braided underlying chassis and an outer polymer sheath 13 in which a "strip" of braid is exposed directly above slot 104, whereby guidewire lumen 18 lies immediately below the exposed strip 33 of braid 31. A clinician may then use the back end of a guide wire to part the braid filaments at any suitable user-defined position along this strip 33, thus exiting the guidewire from catheter 10 through the selected interstice of braid 31.

Figure 4D:
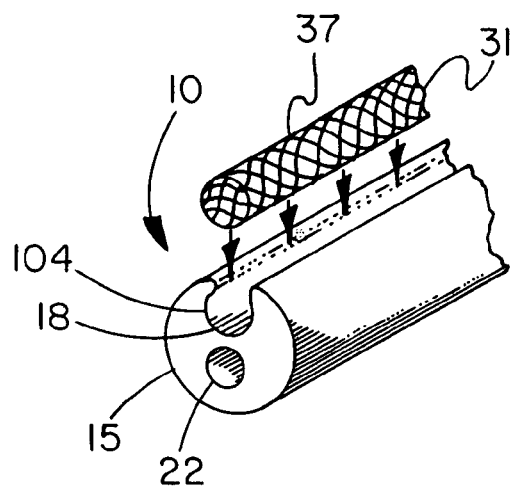
FIG. 4D is a perspective view of catheter shaft with an alternative braid-covered slot wherein a braided tube is fitted and secured into the slot.

FIG. 4D describes an alternative embodiment whereby a braided tube 37 is procured, this tube having an outside diameter corresponding to the inside diameter of slot 104 of catheter shaft 15. The braided tube 37 is made to have a suitable inside diameter to provide adequate clearance for passage therethrough of an intended guidewire. Braided tube is fitted into slot 104 by interference, or by joining with an adhesive. In use, as with the previously described braided construct, the guidewire may be passed through any desired interstice of the braid 31 to exit catheter 10.

Figure 4E:
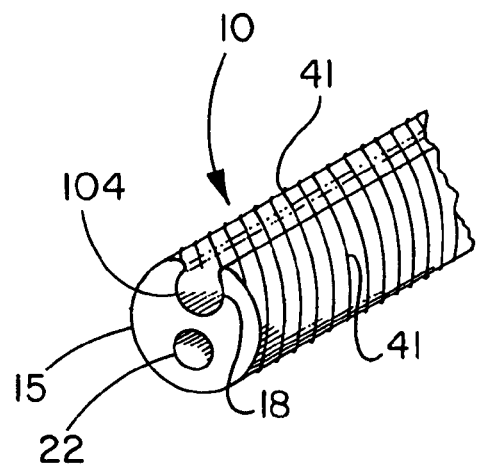
FIG. 4E is a variation of FIG. 4A wherein the braided tubular cover is replaced with a helically wound tubular cover.
Figure 4F:
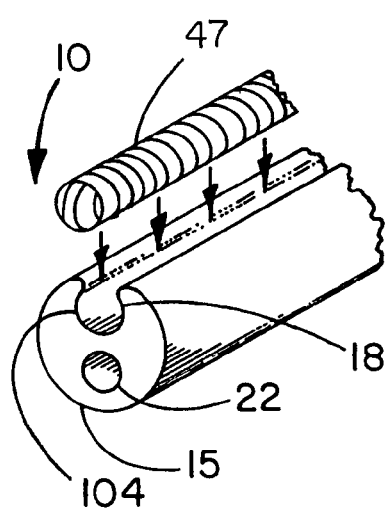
FIG. 4F is a variation of FIG. 4D wherein the braided tube is replaced with a helically wound tube.

FIG. 4E describes a variation of FIG. 4A wherein braid 31 is replaced by helically wound filament 41, which may be of polymeric or metallic material. FIG. 4F shows an alternative to FIG. 4D wherein braided tube 37 is replaced by helically wound tube 47. Again, the helically wound tube may be of polymeric or metallic material. The embodiments of FIGS. 4E and 4F are desirable in that the space between adjacent helical windings will widen when the catheter shaft is bent with the exposed winding on the outside of the bend, making it easier to pass the back end of a guidewire through any desired space between adjacent helical windings.

Figure 4G:
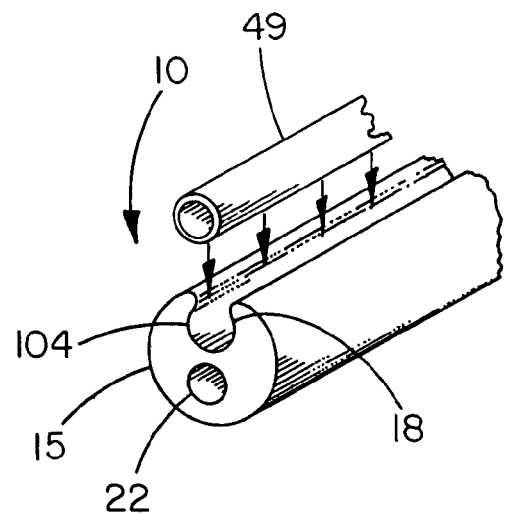
FIG. 4G is a variation of FIGS. 4D and 4F wherein the tubular cover is made from a thin polymeric material.

FIG. 4G is a perspective view of an alternative embodiment to those shown by FIGS. 4D and 4F wherein tube 49 inserted into slot 104 is made from a thin polymeric material. This tube is preferably made by helically wrapping a thermoplastic-coated ePTFE film about a mandrel of suitable size, bonding the wrapping together to result in a cohesive tube, inserting the tube and mandrel into slot 104 and finally removing the mandrel. Alternatively if desired, the mandrel may be removed from within the tube prior to insertion of the tube 49 into slot 104.

Figure 5:
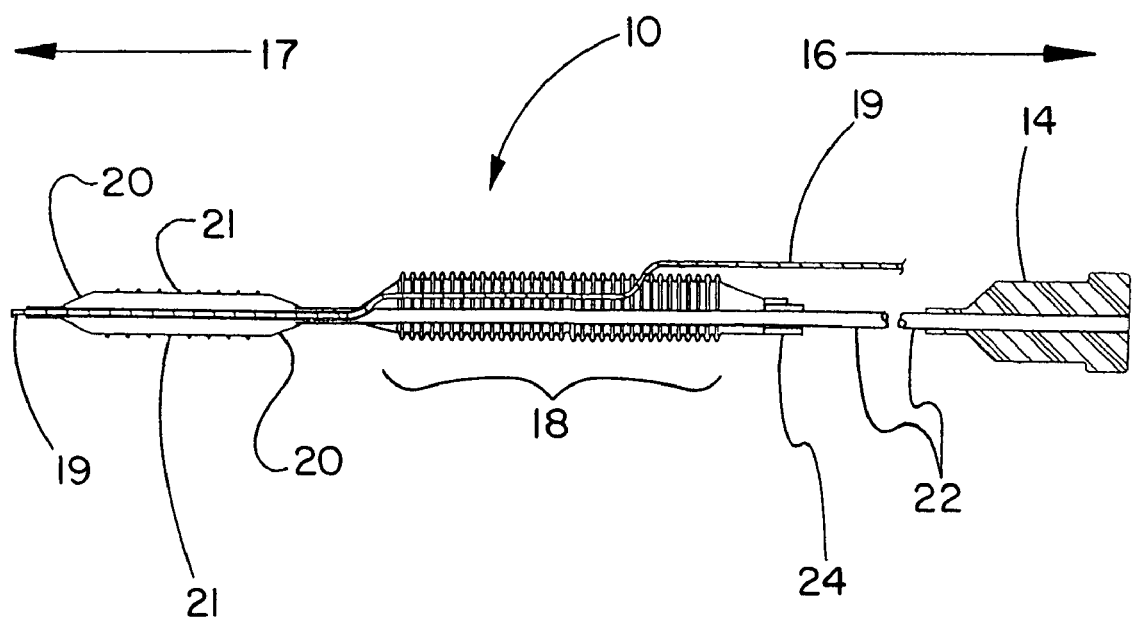
FIG. 5 shows a longitudinal cross section of a basic embodiment of the catheter of the present invention, without a y-fitting but including a hub on the proximal end of the inflation lumen, a puncturable adjustable length guidewire catheter lumen (shown in its axially compressed or shortened state) located distal to the hub and a tubular slider for controlling the proximal end of the adjustable length lumen.

FIG. 5 shows a longitudinal cross section of an alternative embodiment of catheter 10, including a hub 14 on the proximal end 16 of the inflation lumen 22. In this embodiment, catheter 10 is provided with a puncturable adjustable length guidewire lumen 18 that is in the form of a thin tubular sheath 13 puncturable by guidewire 19 as shown. A tubular slider 24 is used in place of a conventional y-fitting, distal to hub 14 for attachment and control of the proximal end of the adjustable length guidewire catheter lumen 18. Adjustable length guidewire catheter lumen 18 is shown in its axially compressed or shortened state. Tubular slider 24 is provided with only a small clearance between the inner diameter of slider 24 and the outer diameter of the inflation lumen 22. Adjustable length guidewire catheter lumen 18 may be made from a variety of thin, flexible polymer materials such as polyethylene, polypropylene, polyamide, polyethylene terephthalate, etc. Porous polymers, optionally provided with a thin, nonporous coating, may be advantageously used because of their excellent flexibility. Adjustable length guidewire catheter lumen 18 is preferably made from a porous expanded PTFE (ePTFE) film that has been provided with a porous or nonporous coating of a thermoplastic fluoropolymer as described previously.

The thin-walled tube is preferably made from an FEP-coated ePTFE film that has been cut into a tape (width, e.g., 12.7 mm) and helically wrapped on a mandrel with the FEP coating placed on the exterior of the wrapping. The helically wrapped tube is then placed into an oven for a suitable time (e.g., 8 minutes in an oven set at a temperature of 320° C.) to thermally bond the overlapped edges of the helical wrapping together, thereby forming a coherent tube. After removal from the oven and cooling, the resulting tube is removed from the mandrel and may be used as the adjustable length lumen component in the catheter of the present invention. The ends of this tube may be joined to the adjacent components by overlapping the tube end over the adjacent component and adhering the overlapped areas with an adhesive such as a cyanoacrylate (e.g., Loctite 401, Rocky Hill, Conn.) or an ultraviolet adhesive (e.g., Loctite 3311). Alternatively, the tube may be everted to orient the FEP-coating toward the lumen, and an adequate heat source may be used to melt-bond the FEP coating to catheter components such as metal hypotubes.

For use as the puncturable, adjustable length lumen tubular component of a catheter, the ePTFE tube may be provided with corrugations (e.g., accordion pleats or folds) with various methods such as those taught by U.S. Pat. No. 3,105,492 to Jeckel and U.S. Pat. No. 6,016,848 to Egres, Jr. Alternatively, it is not required to provide the thin-walled tube with pre-formed corrugations as, during axial compression from the fully extended length to the shortened, fully compressed length, the tube will wrinkle and corrugate in a non-uniform but entirely suitable manner for use as the adjustable length lumen portion 18 of catheter 10. In another alternative, an elastomer may be used for the adjustable length portion 18 that would be in its relaxed state prior to loading over the guidewire and would extend into a tensioned condition when the distal end of the catheter is advanced.

Longitudinally extruded and expanded tubes of PTFE, that is, seamless ePTFE tubes, may be used in thinwall form as the puncturable, adjustable length guidewire catheter lumen. Under axial compression, the interconnecting fibrils of the node-and-fibril microstructure of ePTFE will progressively bend and fold. This allows the tubular material to axially compress in a substantially uniform fashion, retaining the longitudinal uniformity of the tube wall (macroscopically), without corrugations. This bending of the fibrils within the microstructure of the wall of the ePTFE tube during axial compression is described in U.S. Pat. No. 4,877,661 to House et al. Longer mean fibril length tubes are preferred to maximize the compressible length, e.g., ePTFE tubes of about 50 micron or greater mean fibril length.

A catheter having a puncturable, adjustable length guidewire lumen was constructed using a very thin walled (e.g., 0.03 mm) sheath material. The sheath material is required to be thin enough to corrugate in small folds, allowing the length of the sheath to be reduced to less than 50% of its original length by compressing into the small amplitude folds. A 0.01 mm thick ePTFE film provided with a non-porous FEP coating on one side was chosen for the sheath material. This film was slit to a 6.4 mm width, thereby forming a tape.

An ePTFE tube, having an inner diameter of about 1.6 mm and a wall thickness of about 0.13 mm, was fitted over a 1.6 mm diameter stainless steel mandrel having a length of about 180 cm. The 6.4 mm wide tape was then helically wrapped about the outer surface of the ePTFE tube with a 50% overlap, resulting in a helically-wrapped tube covered with two layers of tape. The resulting assembly was then placed into an air convection oven set at 320° C. for 8 minutes, after which it was removed from the oven and allowed to cool in an ambient environment.

After cooling, the helically-wrapped tube was removed from the mandrel by withdrawing the mandrel from the tube. The end of the extruded tube that had not been helically-wrapped was clamped in a vise. The end of the helical wrapping closest to the vise was simultaneously pinched on opposite sides of the tube using the thumb and forefingers of both hands, and the helical-wrapping was stripped from the underlying ePTFE tube by everting the helically-wrapped tube while pulling it away from the vise.

This thin-walled tube had an approximate wall thickness of 0.03 mm (measured using Mitutoyo Snap Gauge, Model #1D-C112EBS) and an inner diameter of approximately 1.7 mm (measured using a certified minus pin gauge with a tolerance of 0.01 mm). When this tube was loaded on a 1.2 mm diameter mandrel, it was able to be easily compressed to about 5% of its original length using light digital pressure.

Continuing assembly of the catheter, this sheath was then coaxially mounted over a conventional Percutaneous Transluminal Coronary Angioplasty (PTCA) catheter with a maximum outer diameter proximal of the balloon of less than approximately 0.040" (1.02 mm). The PTCA catheter used was a rapid exchange type, having a proximal guidewire exit port at a location significantly distal of its hub. Prior to mounting the sheath, a 9 Fr (3.0 mm) inner diameter hemostasis y-arm valve (P/N 80348, Qosina, Edgewood, N.Y.) was slid onto the catheter from the catheter's distal end (hemostasis valve oriented away from the back end of the catheter). Next, a female luer (P/N 65206. Qosina, Edgewood, N.Y.) was slid onto the catheter and the luer connection of these two components was engaged. A 2.0 mm inside diameter by 2.1 mm outside diameter 304 stainless steel tube (Microgroup, Medway, Mass.) was then swaged down to approximately 1.4 mm inside diameter by 1.6 mm outside diameter, and then trimmed to a length of approximately 19 mm.

This tube was slid coaxially over the catheter and bonded to the distal end of the female luer with an approximate 6 mm overlap using cyanoacrylate adhesive (Loctite 401, Loctite Corp., Rocky Hill, Conn.). Next, the helically-wrapped sheath described above was slid over the distal tip of the catheter and its proximal end attached by sliding it over the exposed end of the hypotube. These overlapped surfaces were bonded using the cyanoacrylate adhesive, after which 2.3 mm inside diameter polyolefin 2-to-1 shrink ratio shrink tubing was fitted over the junction and heated to conform to the surface of the junction. The distal end of the sheath was then trimmed to a length of approximately 135 cm, equal to the desired working length of the catheter (i.e. length from the distal tip of the catheter to the distal end of the strain relief on the catheter's hub). The distal end of the sheath was then attached at a location approximately 2 mm distal of the proximal guidewire port in the wall of the PTCA catheter. This attachment was made using the cyanoacrylate adhesive between the sheath and catheter, and then over-wrapping this attachment point with cyanoacrylate adhesive and 0.13 mm diameter ePTFE suture (CV-8, WL Gore and Associates, Flagstaff, Ariz.).

To complete the catheter a hemostasis y-fitting was slid distally on the catheter until it was just proximal of the proximal hole of the original PTCA catheter. This compressed the sheath to approximately 15% of its original approximately 135 mm length. A guidewire was then fed into the distal tip of the catheter and carefully threaded through the catheter, including the sheath component, and out from the proximal end of the catheter through the side arm of the y-fitting.

With the guidewire inserted, the user was able to hold the guidewire and hemostasis y-fitting in a fixed position while advancing the distal tip of the catheter relative to the guidewire. Compared to a standard catheter with a proximal guidewire side port fixed distally of the proximal hub, this inventive catheter significantly improved the ability of the section of the catheter, distal to the hemostasis y-fitting, to track the guidewire and allow push forces applied to the proximal portion of the catheter shaft to be transferred directly to the distal tip of the catheter.

Figure 6:
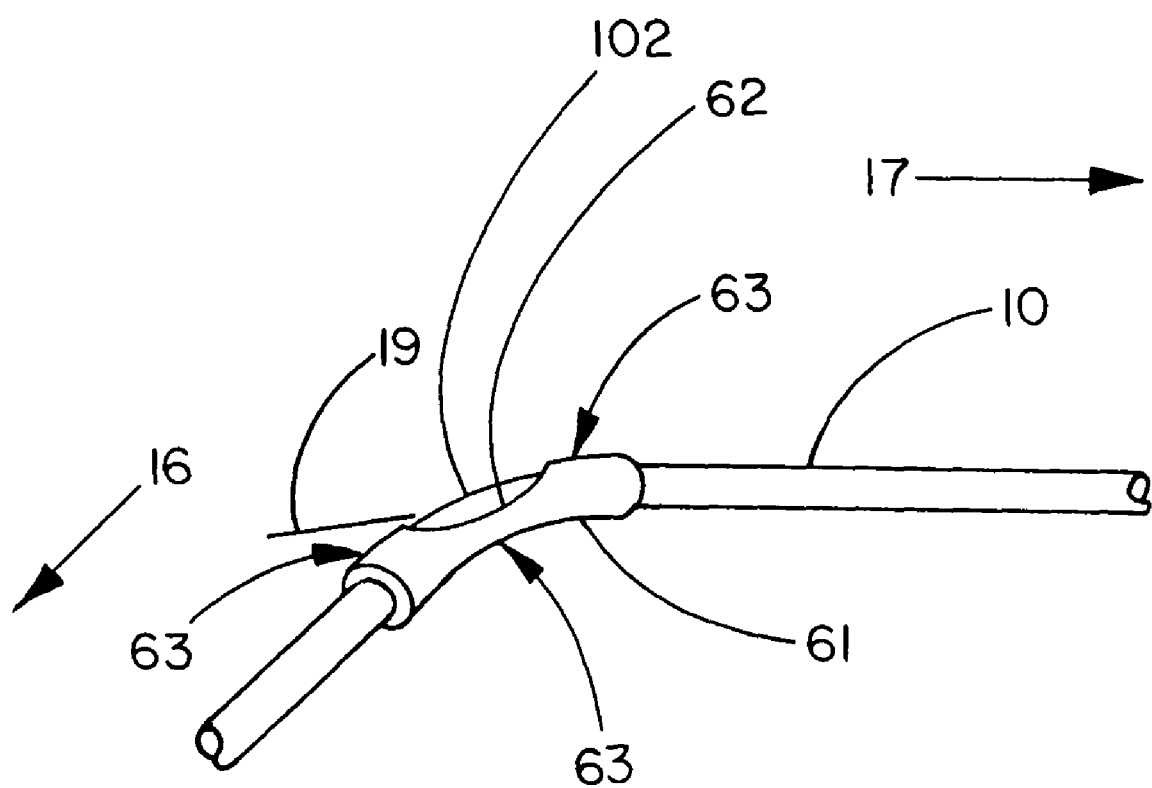
FIG. 6 is a perspective view of a tool useful for bending of the catheter shaft during puncturing of the thin puncturable cover by the back end of a guidewire.

FIG. 6 is a perspective view of catheter 10 in use with a puncturing tool 63 that enables puncturing of the cover 102 by the back end of guidewire 19. While such a tool is deemed unnecessary for many applications, for others it may prove advantageous. As shown, tool 63 is simply a short length of tubing that may be either polymeric tubing or metallic tubing. It is most easily made by bending the short length of tubing (before it is fitted about a catheter) and cutting away a portion of the wall along one side of the tube in the region of the middle of the length of the tube, resulting in opening 62. In use, tool 61 is fitted coaxially about catheter 10 and moved along the length of catheter 10 to the location at which it is desired to puncture cover 102 with the back end of guidewire 19. The tool 61 is oriented so that the opening 62 exposes cover 102 on the side of the catheter where the guidewire is or will be contained. When a guidewire 19 is inserted into the catheter 10 to the location at which it is desired to puncture the catheter, with this location exposed at opening 62 in tool 61, both the catheter 10 and tool 61 are bent as shown by FIG. 6. This bending results in puncturing of cover 102 by the back end of guidewire 19. The bending of catheter 10 is the result of force applied at three points 63, with the middle point being on the inside of the bend along the middle of the length of the bend and the two outer points being on the outside of the bend at the two opposite ends of the bend. It is apparent that the tool may take any suitable form that provides this three point contact during bending wherein the act of bending enables or results in puncturing of cover 102 at the desired location by the back end of guidewire 19. Following puncture, the tool is moved out of the way by sliding it coaxially along the length of the guidewire.

While the principles of the invention have been made clear in the illustrative embodiments set forth herein, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

We claim:

1. A catheter assembly comprising a flexible catheter shaft having a length and an outer surface, and having at least one longitudinally oriented slot extending along at least a portion of the length of said catheter shaft, wherein said slot is provided with an outer cover consisting essentially of a helically wrapped porous polytetrafluoroethylene tape whereby said covered slot provides a lumen extending along the portion of the length of the catheter shaft, said cover adhered to the outer surface of the catheter shaft adjacent to the slot, said cover being puncturable at multiple points along the length by the back end of a guidewire, said cover being resistant to tearing by the guidewire at a puncture site following having been punctured by the guidewire.

2. A catheter assembly according to claim 1 wherein said helically wrapped tape comprises two layers with the two layers applied at different wrap angles.

3. A catheter assembly according to claim 1 wherein said porous polytetrafluoroethylene is provided with a non-porous coating.

4. A catheter assembly according to claim 3 wherein said cover is translucent.

5. A catheter assembly according to claim 1 wherein said cover is translucent or transparent wherein a guidewire located within the slot is visible through the cover.

6. A catheter assembly according to claim 1 wherein said lumen is a guidewire lumen.

7. A catheter assembly according to claim 1 wherein said lumen extends for most of the length of the catheter.

8. A catheter assembly according to claim 1 wherein said lumen extends for all of the length of the catheter.

* * * * *